United States Patent
Papadopoulos (10) Patent No.: US 9,949,486 B2
(45) Date of Patent: Apr. 24, 2018

(54) AGROCHEMICAL COMPOSITION COMPRISING A N,N#-DISUBSTITUTED (THIO)UREA FOR THE IMPROVEMENT OF CROP PRODUCTIVITY

(71) Applicant: Crop Intellect Ltd., Lincoln (GB)

(72) Inventor: Apostolos Papadopoulos, Lincoln (GB)

(73) Assignee: Crop Intellect Ltd., Lincoln (GB)

(*) Notice: Subject to any disclaimer, the term of this patent is extended or adjusted under 35 U.S.C. 154(b) by 0 days.

(21) Appl. No.: 15/111,347

(22) PCT Filed: Jan. 14, 2015

(86) PCT No.: PCT/GB2015/050059
§ 371 (c)(1),
(2) Date: Jul. 13, 2016

(87) PCT Pub. No.: WO2015/107336
PCT Pub. Date: Jul. 23, 2015

(65) Prior Publication Data
US 2016/0330963 A1    Nov. 17, 2016
US 2017/0172148 A9    Jun. 22, 2017

(30) Foreign Application Priority Data
Jan. 14, 2014  (GB) .................... 1400557.3

(51) Int. Cl.
| | | |
|---|---|---|
| *A01N 47/30* | (2006.01) | |
| *A01N 59/06* | (2006.01) | |
| *A01N 37/46* | (2006.01) | |
| *C05D 9/02* | (2006.01) | |
| *C05C 1/00* | (2006.01) | |
| *A01N 59/16* | (2006.01) | |

(52) U.S. Cl.
CPC ............. *A01N 47/30* (2013.01); *A01N 37/46* (2013.01); *A01N 59/06* (2013.01); *A01N 59/16* (2013.01); *C05C 1/00* (2013.01); *C05D 9/02* (2013.01)

(58) Field of Classification Search
CPC ........ A01N 47/30; A01N 59/16; A01N 37/46; A01N 59/06; C05D 9/02; C05C 1/00
See application file for complete search history.

(56) References Cited

U.S. PATENT DOCUMENTS 5,177,008 A * 1/1993 Kampen .............. C12F 3/10
                                                        435/139
2008/0307845 A1* 12/2008 Marks ............... A01N 47/30
                                                        71/28

FOREIGN PATENT DOCUMENTS

| CN | 102303990 A | 1/2012 |
|---|---|---|
| CN | 102887802 A | 1/2013 |
| CN | 103232305 A | 8/2013 |
| CN | 103319237 A | 9/2013 |
| CN | 103408349 A | 11/2013 |
| CN | 103896672 A | 7/2014 |
| GB | 2086228 A | 5/1982 |
| WO | WO83002546 | 8/1983 |

OTHER PUBLICATIONS

Ku, X, et al., Effect of poly(gamma-glutamic acid) on Wheat Productivity, Nitrogen Use Efficiency and Soil Microbes, 2013, Journal of Soil Science and Plant Nutrition, vol. 13, Issue 3, pp. 744-755.*
Borowski, E., & Michalek, S. (2010). The effect of foliar nutrition of spinach (*Spinacia oleracea* L.) with magnesium salts and urea on gas exchange, leaf yield and quality. Acta Agrobotanica, 63(1).
Cerdán, M. et. al. (2013). Effect of commercial amino acids on iron nutrition of tomato plants grown under lime-induced iron deficiency. Journal of Plant Nutrition and Soil Science, 176(6), 859-866.
GB Search and Exam Report dated Jul. 15, 2014.
GB Examination Report dated Dec. 17, 2014.
Mahgoub, M.H. et. al. (2011). Growth parameters, yield and chemical composition of Matthiola incana plants as influenced by foliar spray with stigmasterol and diphenylurea. J Appl Sci Res 7 (11): 1575-1582.
Mazher, A. A. et. al. (2011). Effect of Kinetin, Ascorbic Acid and GlutamicAcid on Growth and Chemical Constituents of *Codiaeum variegatum* L. Plants, American-Eurasian J. Agric. & Environ. Sci, 10, 318-323.
El-Metwally, A. E. et. al. (2010). Response of wheat to magnesium and copper foliar feeding under sandy soil condition. J Am Sci, 6, 818-823.
Oertli, J. J., & Jacobson, L. (1960). Some quantitative considerations in iron nutrition of higher plants. Plant physiology, 35(5), 683.

(Continued)

*Primary Examiner* — John Pak
*Assistant Examiner* — Andriae M Holt
(74) *Attorney, Agent, or Firm* — Dinsmore & Shohl LLP (57) ABSTRACT

The invention relates to an agrochemical composition containing a compound of formula (1), a glutamic acid compound, and a source of magnesium and/or a source of iron. The composition applied e.g. foliarly has demonstrated synergistic benefits that improve crop yields and quality characteristics.

Formula (1)

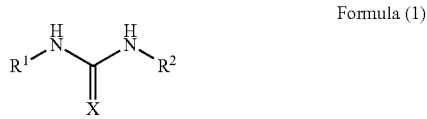

4 Claims, 1 Drawing Sheet

(56) References Cited

OTHER PUBLICATIONS

Piotrowska, A., & Czerpak, R. (2009). Cellular response of light/dark-grown green alga Chlorella vulgaris Beijerinck (Chlorophyceae) to exogenous adenine-and phenylurea-type cytokinins. Acta physiologiae plantarum, 31(3), 573-585.
Taiz, L., & Zeige, E. (2002). Topic 7.11, Chlorophyll Biosynthesis. Plant Physiology Online (HTTP). a companion to Plant Physiology. Sinauer Associates. Archived from the original on Dec. 7, 2006.
XP002737355_Thomson_Scientific, (1999).

* cited by examiner

AGROCHEMICAL COMPOSITION COMPRISING A N,N#-DISUBSTITUTED (THIO)UREA FOR THE IMPROVEMENT OF CROP PRODUCTIVITY

CLAIM OF PRIORITY

This application is the United States National Phase filing of PCT/GB2015/050059 filed Jan. 14, 2015, which claims the benefit of earlier filed Great Britain Application GB1400557.3 filed Jan. 14, 2014, the entire contents of which are incorporated herein by reference.

The present invention relates to agrochemical compositions and the use of ingredients to improve plant physiology.

BACKGROUND TO THE INVENTION

Applications of plant nutrients are regularly made with aim to improve plant's yield and quality. Great efforts are made to concentrate compositions in terms of nutrients without fully understanding nutrient interactions and uptake efficiency by plants. In most instances fertiliser compositions are diluted in water and sprayed on plant's foliage or applied to the soil with the hope that they will be available for uptake by the plants. The mechanisms of nutrient uptake by plants is still under research and very little is known as to how the plant regulates nutrient absorption throughout its lifecycle with temporal variation of nutrient interactions at the different growth and development stages.

Plant nutrition alone can only achieve what is potential by the plant (not considering other contributing parameters such as crop protection and abiotic stresses) and most crop nutrition formulations are not providing nutrients adequately as they are typically applied on a hit-and-miss basis without understanding or affecting the plant nutrient absorption mechanisms. Therefore, the potential of the plant to produce is not achieved or improved.

Cytokinins have been shown to have effects on many physiological and developmental processes, including leaf senescence, nutrient mobilization, apical dominance, the formation and activity of shoot apical meristems, floral development, the breaking of bud dormancy, and seed germination. Cytokinins also appear to mediate many aspects of light-regulated development, including chloroplast differentiation, the development of autotrophic metabolism, and leaf and cotyledon expansion.

Cytokinins work typically in the presence of auxins and the most common first cytokinins are known as zeatin (natural) and kinetin (synthetic) regulating cell activities within the plant. Some synthetic compounds can mimic or antagonize cytokinin action. Cytokinins are defined as compounds that have biological activities which include the ability to do the following, i. induce cell division in callus cells in the presence of an auxin, ii. promote bud or root formation from callus cultures when in the appropriate molar ratios to auxin, iii. delay senescence of leaves and iv. promote expansion of dicot cotyledons.

Nearly all compounds active as cytokinins are N6-substituted amino-purines, such as benzyladenine (BA).

Benzyladenine
(benzylaminopurine)
(BA)

All the naturally occurring cytokinins are aminopurine derivatives. There are also synthetic cytokinin compounds that have not been identified in plants, such as thidiazuron, which is used commercially as a defoliant and an herbicide. It is also known that some molecules act as cytokinin antagonists. These molecules are able to block the action of cytokinins, and their effects may be overcome by the addition of more cytokinin.

Cytokinins can stimulate or inhibit a variety of physiological, metabolic, biochemical, and developmental processes when they are applied to higher plants, and it is increasingly clear that endogenous cytokinins play an important role in the regulation of these events in the intact plant. Cytokinins are also responsible for delaying senescence in leaves and alter the source-sink relationship of nutrients.

$Mg^{2+}$ is essential for plant growth and the amounts of $Mg^{2+}$ vary in different parts of the plant. Excess $Mg^{2+}$ may be stored in vascular cells and in times of starvation $Mg^{2+}$ is redistributed typically from older to newer leaves. When $Mg^{2+}$ is taken up into plants via the roots which carry a great number of negative charges (key to the uptake of cations by root cells), due to the $Mg^{2+}$ binding relatively weakly to these charges, it can be displaced by other cations, impeding uptake and causing deficiency in the plant. Within individual plant cells the $Mg^{2+}$ requirements are largely the same as for all cellular life; $Mg^{2+}$ is used to stabilise membranes, is vital to the utilisation of ATP, is extensively involved in the nucleic acid biochemistry, and is a cofactor for many enzymes (including the ribosome). Also, $Mg^{2+}$ is the coordinating ion in the chlorophyll molecule. It is the intracellular compartmentalisation of $Mg^{2+}$ in plant cells that leads to additional complexity. Four compartments within the plant cell have reported interactions with $Mg^{2+}$. Initially $Mg^{2+}$ will enter the cell into the cytoplasm (by an as yet unidentified system), but free $Mg^{2+}$ concentrations in this compartment are tightly regulated at relatively low levels and so any excess $Mg^{2+}$ is either quickly exported or stored in the second intracellular compartment, the vacuole.

When a $Mg^{2+}$ ion has been absorbed by a cell requiring it for metabolic processes, it is generally assumed that the ion stays in that cell for as long as the cell is active. In vascular cells this is not always the case; in times of plenty $Mg^{2+}$ is stored in the vacuole, takes no part in the day-to-day metabolic processes of the cell, and is released at need. But for most cells it is death by senescence or injury that releases $Mg^{2+}$ and many of the other ionic constituents, recycling them into healthy parts of the plant. Additionally, when $Mg^{2+}$ in the environment is limiting, some species are able to mobilise $Mg^{2+}$ from older tissues. These processes involve the release of $Mg^{2+}$ from its bound and stored states and its transport back into the vascular tissue, where it can be distributed to the rest of the plant. In times of growth and development $Mg^{2+}$ is also remobilised within the plant as source and sink relationships change. $Mg^{2+}$ is the coordinating metal ion in the chlorophyll molecule and in plants where the ion is in high supply about 6% of the total $Mg^{2+}$ is bound to chlorophyll. Thylakoid stacking is stabilised by $Mg^{2+}$ and is important for the efficiency of photosynthesis.

It is an object of the present invention to provide an improved agrochemical composition.

It is an object of the present invention to provide agrochemical compositions that increase crop yield and/or crop quality characteristics.

It is an object of the present invention to improve plant physiology.

It is an object of the present invention to provide agrochemical compositions that increase chlorophyll levels in plants.

It is a further object of the invention to provide agrochemical compositions that increase the photosynthetic rate in plants.

It is a further object of the invention to provide agrochemical compositions that increase foliar absorption of plant nutrients such as magnesium and/or iron.

It is yet a further object of the invention to provide agrochemical compositions that balance the phytohormonal activity of plants which optimise crop physiological characteristics.

DESCRIPTION OF THE INVENTION

The invention relates to agrochemical compositions, and the use of such compositions to increase crop yields, for example by balancing the plant's phytohormones to optimise growth and development efficiency and nutrient uptake efficiency.

The present invention provides knowledge towards positively affecting the absorption of nutrients to increase plant productivity. This is achieved by an improved understanding of the plant's nutrient absorption mechanism. For example, the present invention increases utilisation of $Mg^{2+}$ by releasing the stored $Mg^{2+}$ within the plant for redistribution (cytosolic) and replacing the stored $Mg^{2+}$ in the vacuoles by altering the source-sink relationship.

The invention discloses how the plant's potential to produce is enhanced. Furthermore, with a synergistic effect, utilising a cytokinin balancer, the crop physiological characteristics are optimised towards maximising the crop's potential to perform in terms of yield and quality. In one embodiment, the invention is contained in a scientifically prepared nutrient formulation to promote significant increase in yield and quality in both monocotyledonous and dicotyledonous plants. The time of application of the invention is also critical for achieving maximum potential.

In a first aspect, the invention provides the use of a compound of formula (I)

wherein X is selected from O and S;
$R^1$ and $R^2$ are independently selected from aryl substituted with 0-3 $R^6$, $C_{3-10}$ cycloalkyl substituted with 0-3 $R^6$, a 5-10 membered heterocyclic ring system containing 1-4 heteroatoms independently selected from N, S, and O substituted with 0-3 $R^6$, and $—(CH_2)_{1-3}R^3R^4$;

$R^3$ is selected from aryl substituted with 0-3 $R^6$, $C_{3-10}$ cycloalkyl substituted with 0-3 $R^6$, and a 5-10 membered heterocyclic ring system containing 1-4 heteroatoms independently selected from N, S, and O substituted with 0-3 $R^6$;
$R^4$ is selected from aryl substituted with 0-3 $R^6$, $C_{3-10}$ cycloalkyl substituted with 0-3 $R^{10}$, a 5-10 membered heterocyclic ring system containing 1-4 heteroatoms independently selected from N, S, and O substituted with 0-3 $R^6$, $—(CH_2)_{0-5}CH_3$, $—O(CH_2)_{0-5}CH_3$, $—(CH_2)_{0-6}—OH$, $—(CH_2)_{0-6}—NH_2$, and $—(CH_2)_{0-6}—CO_2R^5$;
$R^5$ is selected from H and $C_{1-6}$ alkyl; and
each $R^6$ is independently selected from H, F, Br, Cl, I, $C_1$-$C_4$ alkyl, phenyl, $CH_2OH$, $CH_2OCH_3$, $C_1$-$C_4$ alkoxy, $C_1$-$C_4$ haloalkyl, $—NR^7R^8$, $—C(\!=\!O)R^8$, $CH_2COOR^8$, or $OR^8$; and
$R^7$ and $R^8$ are independently selected from H and $C_{1-4}$ alkyl;
to improve plant physiology.

In a number of other aspects, the invention provides the use of a compound of formula (1) as defined above or an agrochemical composition of the invention to increase crop productivity and/or crop quality; improve crop physiological characteristics; increase the level of chlorophyll in plants; increase the photosynthetic rate of plants; and/or increase the absorption of magnesium and/or iron by plants.

The invention also relates to the use of compounds of formula (1) or an agrochemical composition of the invention to balance cytokinins in plants (phyto-organisms). In other words, the invention provides the use of a compound of formula (1) or an agrochemical composition of the invention for regulating cytokinin levels in plants. This leads to an improvement in crop physiological characteristics and/or crop yield and quality.

In relation to all aspects of the invention, formula (I) may also represent:

Formula (1)

wherein X is selected from O and S;
$R^1$ and $R^2$ are independently selected from aryl substituted with 0-3 $R^6$, and a 5-10 membered heterocyclic ring system containing 1-4 heteroatoms independently selected from N, S, and O substituted with 0-3 $R^6$;
each $R^6$ is independently selected from F, Br, Cl, I, $C_1$-$C_4$ alkyl, $CH_2OH$, $CH_2OCH_3$, $C_1$-$C_4$ alkoxy, $C_1$-$C_4$ haloalkyl, $—NR^7R^8$, $—C(\!=\!O)R^8$, $CH_2COOR^8$, or $OR^8$; and
$R^7$ and $R^8$ are independently selected from H and $C_{1-4}$ alkyl.

Alternatively, formula (I) may be represented by:

Formula (1)

wherein X is selected from O and S;
$R^1$ and $R^2$ are independently selected from aryl (such as phenyl) substituted with 0-3 $R^6$;
each $R^6$ is independently selected from F, Br, Cl, I, $C_1$-$C_4$ alkyl, $CH_2OH$, $CH_2OCH_3$, alkoxy, $C_1$-$C_4$ haloalkyl, $—NR^7R^8$, $—C(\!=\!O)R^8$, $CH_2COOR^8$, or $OR^8$; and
$R^7$ and $R^8$ are independently selected from H and $C_{1-4}$ alkyl.

$R^6$ may also be independently selected from F, Br, Cl, I, —OH, —OCH$_3$, and C$_1$-C$_4$ alkyl.

In relation to all aspects of the invention, examples of compounds of formula (1) include 1,3-diphenylurea (DPU) and N,N'-diphenylthiourea (DPTU).

Diphenylurea, otherwise known as 1,3-diphenylurea, N,N'-diphenylurea, or carbanilide, has a chemical structure:

Diphenylthiourea, otherwise known as N,N'-diphenylthiourea, 3-diphenyl-2-thiourea, diphenylsulfurea or thiocarbanilide, has a chemical structure:

In a second aspect, the invention provides the use of a compound of formula (1) as described above in combination with a source of magnesium and/or iron.

It has been unexpectedly discovered that the claimed combination of components provides a synergistic effect as measured by lab, field and greenhouse trials. It has been discovered that the application (foliar, soil, seed etc.) of the claimed combination balances plant cytokinins and increases productivity through an increase in the photosynthetic rate. This has never been reported before. Without being bound by theory, it is thought that compounds of formula (1), such as phenyl urea derivatives, balance the plant physiological characteristics which significantly improve yield and quality.

It has also been surprisingly discovered that the further addition of a glutamic acid compounds, for example γ-Polyglutamic acid (γ-PGA) of formula (2), increases the absorption of plant nutrients, such as magnesium and iron, resulting in an increase in their utilisation in the photosynthetic process which improves crop yield further.

The use of the claimed combination of components results in an unexpected increase in crop yield and crop quality characteristics. None of the above components on their own have shown the level of efficacy that is observed when they are employed together, thus demonstrating the synergistic effect of the combinations of the present invention.

Accordingly, the invention also provides the use of a glutamic acid, derivative thereof or degradation product thereof in combination with a source of magnesium and/or iron. This combination may be useful in improving plant nutrient absorption and productivity.

For example, the combination may be used for increasing absorption of magnesium and/or iron in plants; the combination may be used for increasing the level of chlorophyll in plants; the combination may be used for increasing the photosynthetic rate of plants; the combination may be used for increasing crop productivity (yield) and/or crop quality characteristics.

The efficacy of the present invention is further strengthened in a synergistic manner by the addition of a glutamic acid compound, for example a biodegradable biopolymer named gamma-polyglutamic acid (γ-PGA/gama-PGA), which can be obtained with several well reported methods. Glutamic acid compounds such as gamma-PGA and pyroglutamic acid have been found to increase cumulatively Mg and Fe utilisation in a synergistic manner providing the beneficial effects measured by yield and quality in the present invention.

Furthermore, the invention provides an agrochemical composition comprising a glutamic acid compound, a derivative thereof or a degradation product thereof and a source of magnesium and/or iron.

The invention also provides an agrochemical composition comprising (i) a compound of formula (1) as described above, (ii) a glutamic acid compound, a derivative thereof, or a degradation product thereof, and (iii) a source of magnesium and/or iron.

In a further aspect, the invention provides the use of a glutamic acid compound, such as a compound of formula (2) as defined above to increase absorbtion of magnesium and/or iron by plants.

In a further aspect, the invention provides the use of a glutamic acid compound, such as a compound of formula (2) as defined above to increase the level of chlorophyll in plants.

In a further aspect, the invention provides the use of a glutamic acid compound, such as a compound of formula (2) as defined above to increase the photosynthetic rate of plants.

In a further aspect, the invention provides the use of a combination of (i) a glutamic acid compound, such as a compound of formula (2) as defined above, and (ii) a source of magnesium and/or a source of iron to increase the level of chlorophyll in plants.

In a further aspect, the invention provides the use of a combination of (i) a glutamic acid compound, such as a compound of formula (2) as defined above, and (ii) a source of magnesium and/or a source of iron to increase the photosynthetic rate of plants.

In a further aspect, the invention provides the use of a combination of (i) a glutamic acid compound, such as a compound of formula (2) as defined above, and (ii) a source of magnesium and/or a source of iron to increase crop productivity (yield) and/or increase crop quality characteristics.

In a further aspect, the invention provides the use of a glutamic acid, a derivative thereof, or a degradation product thereof to increase the foliar absorption of plant nutrients including but not limited to magnesium and/or iron.

In preferred embodiments of all relevant aspects of the invention, the glutamic acid compound is a polyglutamic acid such as γ-polyglutamic acid (γ-PGA) or pyroglutamic acid. Most preferred is γ-polyglutamic acid.

In preferred embodiments of all relevant aspects of the invention, the compound of formula (1) is diphenylurea or diphenylthiourea, most preferably diphenylurea.

In some embodiments, the glutamic acid compound is a compound of formula (2), i.e. γ-polyglutamic acid (γ-PGA) and the compound of formula (1) is diphenylurea.

The invention may employ a glutamic acid, a derivative of glutamic acid, or a degradation product of glutamic acid. Specific examples include pyroglutamic acid and polyglutamic acids such as γ-polyglutamic acid, as exemplified by formula (2):

Formula (2)

The application of a glutamic acid compound, or a derivative thereof or a degradation product thereof is ideally from 0.01 grams to 10 g per liter of end product adequate to treat at least a hectare, or 0.1 grams to 5 g per liter of end product or more appropriately 0.5 to 1 g per liter of end product.

The invention may also employ a source of magnesium and/or a source of iron.

Suitable sources of magnesium include but are not limited to magnesium nitrate, magnesium chloride, magnesium sulphate, magnesium oxide, magnesium carbonate, magnesium iodide, magnesium acetate, magnesium hydride, magnesium aluminium hydroxide carbonate hydrate, and mixtures thereof. In some embodiments, the composition comprises magnesium sulphate such as magnesium sulphate heptahydrate.

Magnesium is a constituent of chlorophyll and essential for photosynthesis. Chlorophyll absorbs energy from sunlight, which the plant uses to manufacture food in the process of photosynthesis. Plants lacking magnesium have a reduced ability to manufacture chlorophyll, and this has a direct impact on the plant's ability to manufacture its own food. A lack of magnesium therefore slows plant growth. Magnesium is also used within the plant in various metabolic functions; it activates enzymes and helps move phosphorus (another essential plant nutrient) around the plant. Plants need magnesium in relatively large quantities; it is often referred to as a "macro-nutrient." Soil minerals, organic material, fertilizers, and dolomitic limestone are traditional sources of magnesium for plants.

A magnesium compound may be included in a composition of the invention in amount ranging from about 0.1 to about 12% w/w, about 1.0 to about 8% w/w, preferably about 4% w/w.

Suitable sources of iron include but are not limited to iron nitrate, iron chloride, iron sulphate, iron oxide, iron carbonate, iron iodide, iron acetate, iron hydride, iron-EDTA complex, and mixtures thereof. In some embodiments, the compositions of the invention comprise iron sulphate, such as iron sulphate heptahydrate.

Iron deficiency is a limiting factor of plant growth. Iron is present at high quantities in soils, but its availability to plants is usually very low, and therefore iron deficiency is a common problem. Plants can uptake iron in its oxidized forms such as $Fe^{2+}$ (ferrous form) and $Fe^{3+}$ (ferric form), but although most of the iron on the earth crust is in the form of $Fe^{3+}$, the $Fe^{2+}$ form is physiologically more significant for plants. This form is relatively soluble, but is readily oxidized to $Fe^{3+}$, which then precipitates. $Fe^{3+}$ is insoluble in neutral and high pH, making iron unavailable to plants in alkaline and in calcareous soils. Furthermore, in these types of soil, iron readily combines with phosphates, carbonates, calcium, magnesium and hydroxide ions.

An iron compound may be included in a composition of the invention in amount ranging from about 0.01 to about 6.0% w/w, about 0.1 to about 3.0% w/w, preferably about 1% w/w.

In some embodiments, the compositions of the invention comprise magnesium nitrate or sulphate and iron nitrate or sulphate.

Diphenylurea has been studied for its cytokinin effects on plants and mostly for micropropagation for the stimulation of rooting or callus. Cytokinins are known to affect many plant developmental processes including cell division, cell differentiation, chlorophyll senescence and apical dominance. They are structurally related to adenine and are produced by actively growing tissues, particularly roots, embryos, and fruits. Cytokinins are involved in control of cell division and differentiation and this ability of cytokinins to trigger cell division and influence differentiation is related to the fact that cytokinins stimulate RNA and protein synthesis, which may be involved in cell division.

The addition of a cytokinin balancer, such as diphenylurea/diphenylthiourea, to the composition of the invention has shown further improvements in yield, photosynthetic rate and crop physiological balance. In contrast, none of the components on their own have shown the level of benefit as when they are added together demonstrating the synergy resulting in a cumulative effect. The result is an increase of 28.5% in yield in terms of fresh weight and quality characteristics including leaf strength, colour, and shelf-life (reduced rate of water loss and maintenance of hardness).

The cytokinins balancer is suitably present within the composition of the invention in an amount up to 0.01 weight percent. The cytokinin balancer may be present in the composition according to the invention at a concentration in the range of 0.01 to 1000 ppm, and preferably in the range 0.5 to 200 ppm, 1 to 100 ppm, 2 to 20 ppm, most preferably in the range of 5 to 15 pm, e.g. about 10 ppm.

The compositions of the invention may further comprise other conventional agrochemical ingredients such agrochemical nutrients (such as macro and micro nutrients), and agrochemically acceptable excipients. Suitable macro nutrients include but are not limited to sources of nitrogen, phosphorous, potassium, and sulphur. Suitable micro nutrients include but are not limited to sources of magnesium and iron. Others include boron, cobalt, chromium, copper, fluoride, iodine, manganese, molybdenum, selenium, zinc etc.

Accordingly, the compositions of the invention may further comprise one or more agrochemically acceptable excipients. Examples of such components include water, amino acids, vitamins, seaweed and other plants extracts, weak acids, plant oils, essential oils, metabolic stimulating agents, emulsifiers, thickeners, colouring agents, suspension agents, dispersion agents, carriers or excipients and wetting agents.

As used herein, the expression "weak acid" refers to a weak organic acid such as acetic acid, citric acid, humic acid, fulvic acid or propanoic acid; preferably the weak acid is citric acid.

Suitable emulsifiers for use in the compositions of the present invention include any known agriculturally acceptable emulsifier. In particular, the emulsifier may comprise a surfactant such as: fatty alcohol polyethylene glykol ether, typically alkylaryl sulphonates, ethoxylated alcohols, polyalkoxylated butyl ethers, calcium alkyl benzene sulphonates, polyalkylene glycol ethers and butyl polyalkylene oxide block copolymers as are known in the art. Nonyl phenol emulsifiers such as Triton $N_{57}$™ are particular examples of emulsifiers, which may be used in the compositions of the invention, as are polyoxyethylene sorbitan esters such as polyoxyethylene sorbitan monolaurate (sold by ICI under the trade name "Tween™"). In some instances, natural organic emulsifiers may be preferred, particularly for organic farming applications. Coconut oils such as coconut diethanolamide is an example of such an compound. Palm oil products such as lauryl stearate may also be used.

Examples of thickeners which may be present in the compositions of the present invention comprise gums, for example xanthan gum, or lignosulphonate complexes, as are known in the art. In particular, beet molasses provides a good natural thickener, which also acts as a colourant and a source of plant sugars and hormones. The thickener may be present at a concentration in the range of 0.1 to 5.00% w/w, for example in the range of 1.0 to 3.0% w/w, e.g. around 2.0% w/w. Other sources of molasses are also acceptable for use in the invention.

Suitable suspension agents which may be included in the compositions of the present invention include hydrophilic colloids (such as polysaccharides, polyvinylpyrrolidone or sodium carboxymethylcellulose) and swelling clays (such as bentonite or attapulgite).

Suitable wetting agents for use in the compositions of the present invention include surfactants of the cationic, anionic, amphoteric or non-ionic type, as is known in the art.

The agrochemical compositions of the invention may be applied to plants, in particular crop plants, in any conventional manner, e.g. by soil, water, growth medium, seed treatment, gel, fumigation or foliar application: In some embodiments, foliar application is preferred. The agrochemical compositions of the invention may be applied to root systems, stems, seeds, grains, tubers, flowers, fruit, etc. as required. Examples of means of application include spraying, e.g. by means of an electrostatic or other conventional sprayer, or drip irrigation methods or fertigation systems, which involve application directly to the soil, so as to allow magnesium and/or iron uptake through the roots.

The compositions of the invention may be adapted for the means of application, e.g. prepared in a form suited to the required means of application. The compositions of the present invention may take the form of liquid or solid concentrates, which require dilution before application. The compositions may be formed into, for example, water dispersible granules, slow or fast release granules, soluble concentrates, oil miscible liquids, ultra low volume liquids, emulsifiable concentrates, dispersible concentrates, oil in water, and water in oil emulsions, micro-emulsions, suspension concentrates, aerosols, capsule suspensions and seed treatment formulations. Aerosol versions of the compositions may be prepared using a suitable propellant, for example n-butane. The form type chosen in any instance will depend upon the particular purpose envisaged and the physical, chemical and biological properties of the composition. The compositions of the present invention may be prepared using any conventional techniques and methods. Granules may be, for example, formed either by granulating a composition of the present invention alone or with one or more powdered solid diluents or carriers. Granules of the magnesium and/or iron salts may be prepared onto which the cytokinin balancer and γ-PGA may be coated by any suitable conventional means. Dispersible concentrates may be prepared by mixing a composition of the present invention in water or an organic solvent, such as a ketone, alcohol or glycol ether. Suspension concentrates may be prepared by combining the compositions of the present invention in a suitable medium, optionally with one or more dispersing agents, to produce a suspension. One or more wetting agents may be included in the suspension and a suspending agent may be included to reduce the rate of settling or to improve formulation stability.

In a further aspect the present invention, there is provided a formulation for administration to plants or to the environment of plants, the formulation comprising a composition according to the invention and a medium in which the composition may be dispersed or dissolved.

Suitable mediums include any known dispersants or solvents for the composition, for example water or a water miscible liquid, such as [pi]-propanol. The medium is preferably such as to provide formulations that may be used in non-pressurized, hand-actuated spray pumps. The medium is preferably a solvent and most preferably water.

The amount of dispersant or solvent, e.g. water, used will depend upon the particular mode of administration of the formulation and to where it is being applied. In general, a formulation according to the invention may contain from 10-20% v/v of the composition of the present invention with the remainder being dispersant or solvent, e.g. water.

The compositions of the invention are suitable for use on most crops, but in particular can be used for the treatment of greenhouse crops, vegetables, and fruit crops. For example, the compositions of the invention may be used on but not limited to cereals, oil seed rape, potatoes, sugar beet, vegetable crops, leafy vegetables, cucurbits and grassland.

The compositions may be applied to any plant or crop. For example, the compositions may be applied to flowers, and potatoes. However, application to both monocotyledonous and dicotyledonous plants has shown excellent yield and quality benefits.

The amount of composition or formulation applied in any particular situation will vary depending upon a number of factors such as the nature of the crop, location season etc. Applications timings and dosages are important and dependent on plant growth stages.

In some embodiments, the invention discloses the use of a compound of formula (1), such as diphenylurea/diphenylthiourea, applied foliarly and having a positive effect on the plant without the addition of any other components such as plant nutrients. Without being bound by theory, it is believed that the compounds work as a metabolite which balances the cytokinin production. Combination in a synergistic effect with γ-PGA increases Mg and Fe absorption, improves significantly the plant's productivity and quality through plant physiological improvement and nutrient absorption.

The invention will now be particularly described by way of the following non-limiting examples.

DEFINITIONS

As used herein, the term "aryl" is intended to mean phenyl or naphthyl, which when substituted, the substitution can be at any position.

As used herein, the term "heterocycle" or "heterocyclic system" is intended to mean a stable 5- to 7-membered monocyclic or bicyclic 7- to 10-membered bicyclic heterocyclic ring which is saturated partially unsaturated or unsaturated (aromatic), and which consists of carbon atoms and from 1 to 4 heteroatoms independently selected from the group consisting of N, O and S and including any bicyclic group in which any of the above-defined heterocyclic rings is fused to a benzene ring. The nitrogen and sulphur atoms may optionally be oxidized. The heterocyclic ring may be attached to its pendant group at any heteroatom or carbon atom which results in a stable structure. The heterocyclic rings described herein may be substituted on carbon or on a nitrogen atom if the resulting compound is stable. If specifically noted, nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. As used herein, the term "aromatic heterocyclic system" is intended to mean a stable 5- to 7-membered monocyclic or bicyclic or 7- to 10-membered bicyclic heterocyclic aromatic ring which consists of carbon atoms and from 1 to 4 heteroatoms independently selected from the group consisting of N, O and S. It is preferred that the total number of S and O atoms in the aromatic heterocycle is not more than 1.

Examples of heterocycles include, but are not limited to, 1H-indazole, 2-pyrrolidonyl, 2H, 6H-1, 5,2-dithiazinyl, 2H-pyrrolyl, 3H-indolyl, 4-piperidonyl, 4aH-carbazole, 4H-quinolizinyl, 6H-1, 2,5-thiadiazinyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazalonyl, carbazolyl, 4aH-carbazolyl, -carbolinyl, chromanyl, chromenyl, cinnolinyl, decahydroquinolinyl, 2H, 6H-1, 5,2-dithiazinyl, dihydrofuro [2,3-b] tetrahydrofuran, furanyl, furazanyl, imidazolidinyl, imidazolinyl, imidazolyl, indolenyl, indolinyl, indolizinyl, indolyl, isobenzofuranyl, isochromanyl, isoindazolyl, isoindolinyl, isoindolyl, isoquinolinyl, isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinylperimidinyl, phenanthridinyl, phenanthrolinyl, phenarsazinyl, phenazinyl, phenothiazinyl, phenoxathiinyl, phenoxazinyl, phthalazinyl, piperazinyl, piperidinyl, pteridinyl, piperidonyl, 4-piperidonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, pyrrolyl, quinazolinyl, quinolinyl, 4H-quinolizinyl, quinoxalinyl, quinuclidinyl, carbolinyl, tetrahydrofuranyl, tetrahydroisoquinolinyl, tetrahydroquinolinyl, 6H-1, 2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, xanthenyl. Preferred heterocycles include, but are not limited to, pyridinyl, furanyl, thienyl, pyrrolyl, pyrazolyl, imidazolyl, indolyl, benzimidazolyl, 1H-indazolyl, oxazolidinyl, benzotriazolyl, benzisoxazolyl, oxindolyl, benzoxazolinyl, or isatinoyl. Also included are fused ring and Spiro compounds containing, for example, the above heterocycles.

The term "substituted", as used herein, means that one or more hydrogens on the designated atom or group is replaced with a selection from the indicated group, provided that the designated atom's or group's normal valency is not exceeded, and that the substitution results in a stable compound. When a substituent is keto (i. e., =O), then 2 hydrogens on the atom are replaced.

As used herein, the term "crop characteristics" refers to, for example, shelf life, chlorophyll levels, leaf number, sugar level (ideally between 9-10% by weight),

EXAMPLES

Example 1

The following composition to produce 1 lt of end product is described as below:

| Ingredient | % w/v | Mass (g) |
|---|---|---|
| γ-PGA | 0.1% | 1 g |
| DPTU/DPU | 10 ppm | 0.01 g |
| Urea | 15% | 347 |
| Magnesium sulphate | 2% | 212 |
| Iron sulphate | 0.3% | 16 |
| Manganese sulphate monohydrate | 0.5% | 16 |
| Boric acid | 0.3% | 18 |
| Zinc sulphate | 0.3% | 15 |
| Copper sulphate | 0.1% | 4 |
| Sodium molybdate | 0.01% | 0.3 |
| Citric acid | 0.1% | 1 |
| Molasses | 2% | 20 |
| Water | ad. 100% | 640 |

The composition was prepared by adding water to a vessel and heating it to at least 45° C. This was then stirred and to it was added citric acid and stirring was continued until the citric acid was dissolved. The diphenyl thiourea solution (dissolved separately was added at 10 ppm) was then added to the mixture, followed by the addition of γ-PGA solution (dissolved in water: 0.1%). Boric acid was then added to the mixture and stirred until dissolution was complete. Thereafter, sodium molybdate and copper sulphate were added to the mixture and stirred until dissolved. Manganese sulphate was then added to the mixture and stirred until dissolution was complete. Following this, magnesium sulphate was added to the mixture. The addition of urea was last and finally, molasses were added to the mixture.

Example 2

| Ingredient | % w/v | Mass (g) |
|---|---|---|
| γ-PGA | 0.1% | 1 g |
| DPTU/DPU | 10 ppm | 0.01 g |
| Urea | 15% | 347 |
| Magnesium sulphate | 2% | 212 |
| Iron sulphate | 0.3% | 16 |
| Copper sulphate | 0.1% | 4 |
| Molasses | 2% | 20 |
| Water | ad. 100% | 725 |

The preparation of the formulation of example 2 was prepared similarly to that of example 1.

Example A

| Ingredient | % w/v | Mass (g) |
|---|---|---|
| γ-PGA | 1% | 10 g |
| DPTU/DPU | 5 ppm | 0.005 g |
| Magnesium sulphate | 2% | 212 |
| Iron sulphate | 0.3% | 16 |
| Citric acid | 0.1% | 1 |
| Molasses | 2% | 20 |
| Water | ad. 100% | 850 |

The preparation of the formulation of example 3 was prepared similarly to that of example 1.

Simpler or more complex formulations have been prepared and checked for compatibility with the components of the invention. Compatibility was also checked with sources of salts to include chlorides, nitrates and sulphates at varying hydration. Compatibility was also checked for separation, settling out, precipitation and shelf-life of end product. Tests of compatibility with other agrochemicals under the categories of pesticides, herbicides, insecticides, fungicides etc were also tested and all results produced positive results proving full compatibility and practicality.

Results

Lettuce, beans, wheat and tomatoes were selected as plants to test the efficacy of the invention. Short term crops were grown in the greenhouse to ensure controlled condition and long term crops were grown outdoors in replicated trials. All relevant parameters to evaluate efficacy were tested including chlorophyll content, sugar levels, Mg and Fe tissue content, yield and quality characteristics. All trials were performed to good experimental practice (GEP) standards with adequate replication to conform to statistical comparisons. Environmental condition were monitored and kept the same between treatments for evaluation. John Innes soil based compost with low nutrient contents was used for the experiments and sieved to ensure uniformity. The applications were made to be applied at the equivalent of 5 lt/ha of end product in 180 lt of water. Treatments were administered foliarly just before runoff point. The magnesium and iron were in the form of Sulphate.

Lettuce Results

| Treatment | *Yield (g) | Chlorophyll (mg/cm$^2$) | Sugar level (%) | Mg content (mg/kg fw*) | Fe content (mg/kg dw**) | Leaf number | Weight loss¯ (%) |
|---|---|---|---|---|---|---|---|
| Mg & Fe | 184 | 0.029 | 5.5 | 462 | 246 | 22 | 28 |
| DPU | 213 | 0.029 | 5.5 | 480 | 254 | 28 | 22 |
| DPU + Mg&Fe | 210 | 0.030 | 6.5 | 524 | 286 | 28 | 19 |
| γ-PGA | 178 | 0.028 | 5.5 | 485 | 273 | 23 | 26 |
| γ-PGA + Mg&Fe | 219 | 0.035 | 7.0 | 549 | 295 | 23 | 24 |
| γ-PGA + DPU | 209 | 0.031 | 7.0 | 548 | 268 | 29 | 23 |
| γ-PGA + DPU + Mg&Fe | 254 | 0.041 | 9.7 | 653 | 340 | 34 | 16 |

*fresh weight (yield st. error ±8)
¯weight loss after 7 days in ambient temperature (indication of shelf life)
**Dry weight Results obtained from the lettuce experiment confirmed that the invention has the ability to synergistically provide greater yield and measurable quality characteristics. The weight of lettuce was significantly increased and this was achieved by increasing the lettuce leaf number as well as chlorophyll sugar level, Mg and Fe tissue content.

Furthermore, the effects included a reduction in water loss which is vital to shelf-life of fresh produce.

Beans Results

| Treatment | *Yield (g) | Chlorophyll (mg/cm$^2$) | Mg content (%) | Fe content (mg/kg) | Leaf diameter (cm) | Internode length |
|---|---|---|---|---|---|---|
| Mg & Fe | 322 | 0.024 | 0.40 | 75 | 6.9 | 7.8 |
| DPU | 364 | 0.025 | 0.42 | 86 | 7.8 | 7 |
| DPU + Mg&Fe | 386 | 0.027 | 0.49 | 94 | 7.8 | 7.1 |
| γ-PGA | 334 | 0.025 | 0.48 | 84 | 7 | 7.5 |
| γ-PGA + Mg&Fe | 367 | 0.030 | 0.45 | 102 | 7 | 7.5 |
| γ-PGA + DPU | 354 | 0.029 | 0.48 | 98 | 7.8 | 7 |
| γ-PGA + DPU + Mg&Fe | 471 | 0.040 | 0.59 | 116 | 9.2 | 6.9 |

*fresh weight of above ground plant at 6 wks (st. error ±10)

Results from the greenhouse trial using beans as the test crop demonstrated the superior efficacy of the invention. Larger plants expressed as weight per plant was observed together with an increase in chlorophyll content, Mg and Fe content in the plant tissue and leaf diameter (which promotes resource capture). A reduction in internode length was also observed which is favourable for many greenhouse and outdoor vegetable crops.

Results from Winter Wheat Trials

Figure 1:
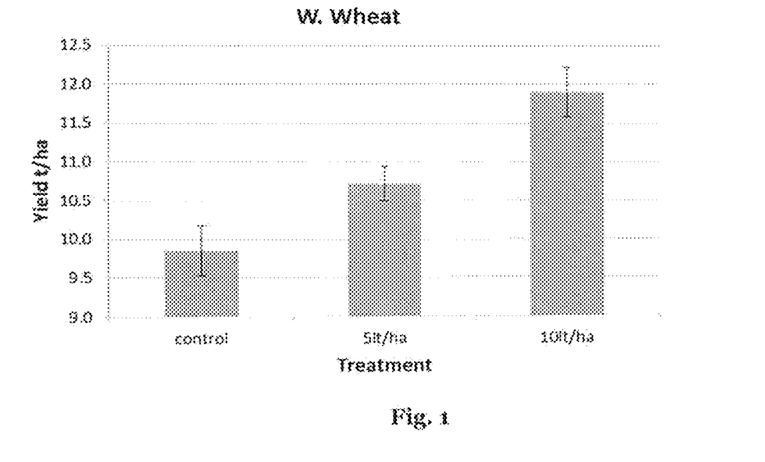
FIG. 1 illustrates the effect on yield in t/ha on winter wheat when agrochemical compositions are administered at 5 lt/ha and 10 lt/ha compared to a control.

The composition prepared as provided in example 1 was used for field tests on winter wheat run by an external consultancy body. Three foliar applications took place at the growth stages T0, T1 and late T2 in 2013 harvest season. Three replicate plots were used for each treatment in a completely randomised design. Applications of the formulation were performed at 5 lt/ha and 10 lt/ha to test the efficacy at different rates. The control treatment was standard farm practice. The results of yield in t/ha on winter wheat are given in FIG. 1.

Figure 2A:
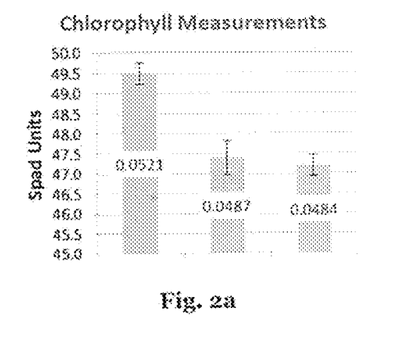
FIG. 2a shows the effect on chlorophyll content achieved by different agrochemical compositions.
Figure 2B:
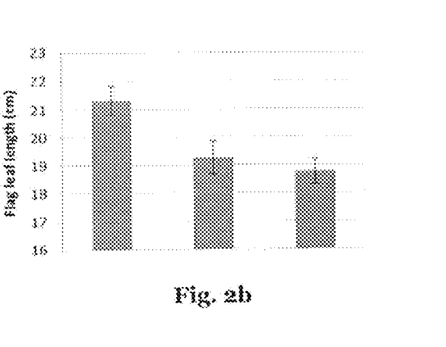
FIG. 2b shows the effect on flag leaf length (cm) achieved by different agrochemical compositions.
Figure 2C:
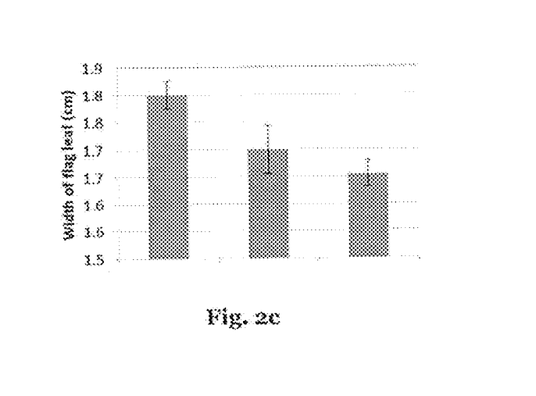
FIG. 2C shows the effect on flag leaf width (cm) achieved by different agrochemical compositions.

The chlorophyll content (Spad Units) and leaf length (Flag leaf length cm) and width (Width of flag leaf cm) results are shown in FIGS. 2a, 2b, and 2C respectively. The values in the bars in FIG. 2a (0.0521, 0.0487, and 0.0484) are the chlorophyll content in milligrams per cm².

A statistically significant increase was measured in terms of yield attributed to the measured increase in chlorophyll (it is believed this is due to the utilisation of Mg and Fe) and the increase in leaf length and diameter which increases resource capture efficiency.

Tomatoes Results

| Treatment | *Yield (g) | Chlorophyll (mg/cm²) | Sugar level (%) | Firmness (turgor MPa) | Internode length |
|---|---|---|---|---|---|
| Mg & Fe | 116 | 0.031 | 6.1 | 0.06 | 10.3 |
| DPU | 132 | 0.031 | 6.8 | 0.08 | 8.1 |
| DPU + Mg&Fe | 138 | 0.035 | 7.1 | 0.08 | 8.2 |
| γ-PGA | 125 | 0.034 | 6.6 | 0.07 | 9.8 |
| γ-PGA + Mg&Fe | 132 | 0.039 | 6.8 | 0.07 | 9.8 |
| γ-PGA + DPU | 138 | 0.034 | 7.3 | 0.08 | 8.2 |
| γ-PGA + DPU + Mg&Fe | 167 | 0.044 | 8.2 | 0.09 | 8.0 |

*average fruit fresh weight

The trial on tomatoes under glass had shown a significant increase in yield and quality characteristics with the application of the present invention. The yield measured as average fruit fresh weight was significantly increased. The chlorophyll and sugar levels was also increased and surprisingly and increase in firmness was also measured. The internode length reduced on average by 20% which is desirable for tomato plants grown under glass due to the infrastructure restrictions and efforts towards vegetative growth.

The invention claimed is:

1. An agrochemical composition, comprising:
   i) 5 ppm diphenylurea having the structure:

ii) 2% w/v magnesium sulphate;
   iii) 0.3% w/v iron sulphate;
   iv) 1% w/v γ-polyglutamic acid having the structure:

and
   v) one or more agrochemically acceptable excipients.

2. The composition of claim 1, wherein the composition comprises one or more agrochemically acceptable excipients selected from the group consisting of water, additional nutrients, growth stimulants, weak acids, plant oils, essential oils, emulsifiers, thickeners, colouring agents, suspension agents, dispersion agents, carriers, and wetting agents.

3. The composition of claim 2, wherein the composition further comprises urea, manganese sulphate, boric acid, zinc sulphate, copper sulphate, sodium molybdate, citric acid, molasses, and water.

4. A method of increasing crop yield or crop quality characteristics comprising the step of applying a composition of claim 1 to plants.

* * * * *

UNITED STATES PATENT AND TRADEMARK OFFICE
CERTIFICATE OF CORRECTION

PATENT NO. : 9,949,486 B2
APPLICATION NO. : 15/111347
DATED : April 24, 2018
INVENTOR(S) : Apostolos Papadopoulos It is certified that error appears in the above-identified patent and that said Letters Patent is hereby corrected as shown below:

On the Title Page

Item (54) and in the Specification Column 1 Lines 1-4 (Title):
Replace "AGROCHEMICAL COMPOSITION COMPRISING A N,N#-DISUBSTITUTED (THIO)UREA FOR THE IMPROVEMENT OF CROP PRODUCTIVITY"
With:
--AGROCHEMICAL COMPOSITION COMPRISING A N,N'-DISUBSTITUTED (THIO)UREA FOR THE IMPROVEMENT OF CROP PRODUCTIVITY--.

Signed and Sealed this
Twenty-ninth Day of May, 2018

Andrei Iancu
*Director of the United States Patent and Trademark Office*